United States Patent [19]

Pohndorf et al.

[11] Patent Number: 4,628,934
[45] Date of Patent: Dec. 16, 1986

[54] METHOD AND MEANS OF ELECTRODE SELECTION FOR PACEMAKER WITH MULTIELECTRODE LEADS

[75] Inventors: Peter J. Pohndorf, Miami Shores; Edward A. Schroeppel, Miramar, both of Fla.

[73] Assignee: Cordis Corporation, Miami, Fla.

[21] Appl. No.: 638,383

[22] Filed: Aug. 7, 1984

[51] Int. Cl.$^4$ .............................................. A61N 1/36
[52] U.S. Cl. .............................. 128/419 PG; 128/786
[58] Field of Search ............... 128/419 P, 419 PG, 786

[56] References Cited

U.S. PATENT DOCUMENTS

| | | | |
|---|---|---|---|
| 3,554,198 | 1/1971 | Tatoian | 128/419 |
| 3,845,773 | 11/1974 | Fontaine et al. | 128/419 P |
| 4,027,678 | 6/1977 | van Oostveen et al. | 128/419 P |
| 4,099,530 | 7/1978 | Chen et al. | 128/419 PT |
| 4,152,540 | 5/1979 | Duncan et al. | 174/152 GM |
| 4,166,470 | 9/1979 | Neumann | 128/419 PG |
| 4,170,999 | 10/1979 | Allen et al. | 128/419 PG |
| 4,187,854 | 2/1980 | Hepp et al. | 128/419 PG |
| 4,192,316 | 3/1980 | Walters et al. | 128/419 PG |
| 4,223,679 | 9/1980 | Schulman et al. | 128/419 PT |
| 4,231,027 | 10/1980 | Mann et al. | 340/636 |
| 4,232,679 | 11/1980 | Schulman | 128/419 PG |
| 4,236,523 | 12/1980 | Gruenewald | 128/419 PT |
| 4,236,525 | 12/1980 | Sluetz et al. | 128/419 P |
| 4,248,238 | 2/1981 | Joseph | 128/419 PG |
| 4,275,737 | 6/1981 | Thompson et al. | 128/419 PG |
| 4,421,114 | 12/1983 | Berkovits et al. | 128/419 PG |
| 4,432,372 | 2/1984 | Monroe | 128/675 |
| 4,462,407 | 7/1984 | Herscovici et al. | 128/419 PG |

FOREIGN PATENT DOCUMENTS 48106  6/1981  European Pat. Off. ..... 128/419 PG

Primary Examiner—William E. Kamm
Attorney, Agent, or Firm—Henry W. Collins; Thomas R. Vigil

[57] ABSTRACT

An electronic electrode switching/selection circuit minimizes the number of feedthroughs from a pacer case to a pacer neck needed to connect with pacing lead electrodes that will be actively used during operation of a pacer. These feedthroughs can be electronically connected with the desired electrode by the physician either at the time of initial implantation or at any time subsequent thereto as may be required. The electronic connection to a feedthrough may be dedicated to a single feedthrough/electrode or electrode pair or the electrodes may be electronically sampled by circuitry in the pacer. The electrode switching/selection circuit may be located in the pacer neck, in an adapter between the pacer neck and a multielectrode lead, or in a multielectrode lead.

Preferably, zener protection diodes are also provided which are connected ahead of the pacing circuitry before or after the electrode switching/selection circuit. These zener protection diodes may be located in the pacer neck, in the adapter, or in the multielectrode lead, according to the location of the electrode switching/selection circuit.

29 Claims, 14 Drawing Figures

METHOD AND MEANS OF ELECTRODE SELECTION FOR PACEMAKER WITH MULTIELECTRODE LEADS

BACKGROUND OF THE INVENTION

1. Field of the Invention

The present invention relates to a cardiac pacemaker or pacer system, especially of the implantable type including a hermetically sealed case for the pacemaker or pacer electronics and a multielectrode pacer lead. More particularly, the invention relates to methods of and means for electrode selection in a pacing system where two multielectrode leads are installed in the pacer at or prior to the time of implantation and not thereafter disturbed.

2. Description of the Prior Art

Heretofore, multielectrode leads have been proposed for cardiac pacemakers wherein several leads are implanted for sensing and pacing functions. After implantation of the leads, tests, such as threshold, are then used to determine the electrodes that appear to the physician to be most satisfactory for the patient and for dedication to the desired function. Also, it is, at times, desirable that all of the leads remain available for use by the physician, especially if the initially selected electrodes fail to continue to function satisfactorily at a later time.

Bringing each lead conductor, however, through a pacer case to a pacer neck separately through individual feedthroughs is expensive and the individual feedthroughs are bulky. As the number of lead conductors is increased, these problems are exacerbated.

Also, Zener protection diodes have been provided within a pacer case and filters have been provided as a part of a feedthrough structure.

Examples of previously proposed pacing systems using multiple electrode leads and diode protection are disclosed in the patents described below:

The Tatoian et al. U.S. Pat. No. 3,554,198 discloses an isolation circuit for a cardiac pacer which is disposed between the pacer and the patient and which is physically external to the pacer. It does not provide any lead selection means or methods.

The Fontaine et al. U.S. Pat. No. 3,845,773 discloses a cardiac pacer wherein a generator is alternately or sequentially connected first with one electrode lead and then to a second electrode lead. Electronic selection of one or more electrodes or electrode pairs of a multielectrode lead as the active element thereof is not disclosed, suggested or illustrated.

The Chen et al. U.S. Pat. No. 4,099,530 discloses a cardiac pacer whose operation can be altered, as by a physician, from a location external thereto through use of magnetic signals. The magnetic signals are not used to effect lead selection.

The Duncan et al. U.S. Pat. No. 4,152,540 discloses a feedthrough connector for use on an implantable cardiac pacer which includes a filter capacitor within the feedthrough connector.

The Neumann U.S. Pat. No. 4,166,470 discloses a cardiac pacer which is powered and controlled through a single receiving antenna and which includes a multiplexer to enable the single antenna to be used for both purposes. Electrodes of a multielectrode lead are not selected with the multiplexer.

The Allen et al U.S. Pat. No. 4,170,999 discloses a cardiac pacer and illustrates what appears to be a zener diode across the output thereof. The diode is internal to the pacer, is not identified by any reference character and is not described in the patent.

The Hepp et al U.S. Pat. No. 4,187,854 discloses a cardiac pacer which is powered and controlled through a single receiving antenna and which includes a multiplexer to enable the single antenna to be used for both control and power reception. Electrodes of a multielectrode lead are not selected with the multiplexer.

The Walters et al U.S. Pat. No. 4,192,316 discloses a cardiac pacer wherein an externally produced multiple bit data word is used to control the pacer timing and mode of operation. No provision is made for electrode selection in a multielectrode lead.

The Schulman U.S. Pat. No. 4,223,679 discloses an implantable tissue stimulator including telemetry means having a signal selection circuit for selecting one of its input signals to be telemetered in accordance with control signals. The selection circuit is not used for selecting electrodes of a multielectrode lead.

The Mann et al U.S. Pat. No. 4,231,027 discloses an implantable tissue stimulator including telemetry means having a signal selection circuit for selecting one of its input signals to be telemetered in accordance with control signals. The selection circuit is not used for selecting electrodes of a multielectrode lead.

The Schulman U.S. Pat. No. 4,232,679 discloses an implantable tissue stimulator which includes a selector and a transmitter with the selector selectively passing to the transmitter signals from any one of sixteen different sources. The selector is not used for selecting electrodes of a multielectrode lead.

The Gruenewald U.S. Pat. No. 3,236,523 discloses a cardiac telemetry system wherein a bistable signal path selector is provided for alternately selecting between a pair of signal path conditions in response to trigger signals. The selector is not used for selecting electrodes of a multielectrode lead.

The Joseph U.S. Pat. No. 4,248,238 relates to a cardiac pacer wherein magnetically actuated switch means are used to selectively connect an atrial lead to either sensing or pulsing circuitry and to selectively connect the pulse generating circuitry to an atrial or a ventricular lead or both. The leads used may be either unipolar with the other electrode on the pacer casing or bipolar with both electrodes at the end of a catheter lead body. The bipolar lead has only two electrodes and provides only a single electrode pair or circuit path.

The Thompson et al. U.S. Pat. No. 4,275,737 discloses a cardiac pacer including two Zener diodes across the output with anodes of a pacing lead being coupled together and cathodes of the lead coupled each to one of the output terminals to protect the pacer, as from electrocautery currents. The diodes are an integral part of the pacer circuitry, and there is no suggestion that they be other than within the pacer case.

The Monroe U.S. Pat. No. 4,432,372 discloses a two lead power/signal multiplexed transducer system in which a piezoresistive pressure transducer is connected to a power source and to electronic processing circuitry by a single pair of leads. Electronic multiplexing circuitry is provided for selectively switching the single pair of leads back and forth between the power source during a power cycle and the processing circuitry during a sensing cycle. This patent is concerned with reducing the number of conductors in a lead as opposed to the number of conductors and conductor feedthroughs in a pacer can or housing.

As will be described in detail hereinafter, in accordance with the present invention, the number of feedthroughs from a sealed cardiac pacer to a pacer neck is limited by providing only enough feedthroughs to connect the electrodes that will be actively used during pacer operation and to provide an electronic electrode switching/selection circuit external to the sealed pacer case to enable these feedthroughs to be electronically connected with the desired electrode by the physician, either at the time of initial implantation or at any time subsequent thereto, as may be required. The electronic connection may be dedicated to a single feedthrough, to an electrode or electrode pair or the electrodes may be electronically sampled by the pacer circuitry. The electrode switching/selection circuit may be located in the pacer neck, in an adapter between the pacer neck and the multielectrode lead, or in the multielectrode lead. Zener protection diodes are preferably provided connected to the electrode conductors before or after the electronic switching/selection circuit. These Zener protection diodes may be located in the pacer neck, in the adapter, or in the multielectrode lead, according to the location of the electrode switching or selection circuit means.

SUMMARY OF THE INVENTION

According to the invention there is provided a cardiac pacing system including: a cardiac pacer having a sealed case with pacer electronic circuitry therein including a pacer system ground, a neck, and at least one feedthrough passing through the sealed case into the neck a pacing lead having a proximal end portion which is received in said neck, a distal end portion, at least two electrodes in the distal end portion and at least two spaced apart terminal connectors in said proximal end portion, said at least one feedthrough being connectable to said terminal connectors, electrode switching/selection circuit means external to the sealed case and connected to said at least one feedthrough between said pacer electronic circuitry and said at least two electrodes for selectively electrically connecting one or more of the electrodes in the pacing lead through said at least one feedthrough with the pacer electronic circuitry.

Further according to the invention there is provided a method for limiting the number of feedthroughs required, for connection to a pacing lead having two or more distal electrodes, in a cardiac pacer, the pacer having a sealed pacer case with pacer circuitry therein, a pacer neck, and at least one feeedthrough extending therethrough, said method comprising at least the steps of: providing a switching/selection circuit means external to the sealed pacer case for coupling the pacer circuitry with the pacing lead; and selectively electrically operating said switching/selection circuit means for selectively electrically connecting said pacer circuitry through said at least one feedthrOugh with one of the electrodes of the pacing lead.

Still further according to the invention there is provided a cardiac pacer system comprising a cardiac pacer unit having a sealed case containing pacer electronics, a pacer neck, and at least one feedthrough extending through said sealed case into said neck, a permanently implantable multielectrode pacing lead having at least two distal electrodes and being adapted to be connected to and used with said pacer unit, and electronic electrode switching/selection circuit means for selectively electrically coupling one or more of the electrodes of said multielectrode pacing lead with said pacer electronics through said at least one feedthrough.

Modern trends toward use of multielectrode leads in implantable cardiac pacemaker or pacer systems have created a problem in design and manufacture of the pacer. The pacer circuitry is generally hermetically sealed within a metal case, both to protect the pacemaker components from invasion or damage by body fluids and, also, to protect the body tissue from any adverse effects from contact with the components themselves. Generally, a separate feedthrough through the hermetically sealed metal case is provided for each electrode lead conductor of a multielectrode lead if that conductor and its associated electrode is to be available for active use. The cost of additional feedthroughs as well as the amount of space taken up by each feedthrough as the number of electrodes is increased make it desirable to keep the number of feedthroughs to a minimum while still having all the electrodes available for active use at some time.

In accordance with the teachings of the present invention, the number of feedthroughs is limited by providing only enough feedthroughs to connect the electrodes that will be actively used at any one time during pacer operation and to provide electronic electrode switching/selection circuitry external to the hermetically sealed pacer case to enable those feedthroughs to be electronically connected with the desired electrode by the physician as may be required.

If all available electrodes are not intended to be used, as for example where only the electrode exhibiting the best threshold is used; or in the case of redundancy, the selection circuitry of the present invention permits dedicating a feedthrough to each such electrode while still using only a minimum number of feedthroughs. Alternatively, a number of the available electrodes may be used without each requiring a dedicated feedthrough since these may be switched to selected feedthroughs on a sampling basis, or on need, under control of the pacer electronics.

In other words, in accordance with the teachings of the present invention, selection may be made either by programming an electronic switching/selection circuit external to the pacer case by a pacer programmer and/or selection may be made by dynamically switching the electronic electrode switching/selection circuit on a sampling basis by the pacer control electronics. The selection signal may, in the first desired instance, originate in the main pacer programming circuit or the selection circuit may itself be capable of directly receiving programming signals from a programmer.

The selection circuit may be located in the pacer neck, in an adapter between the pacer neck and the multielectrode lead, or in the multielectrode lead itself.

Also one or more zener diodes are preferably provided, such as for defibrillation protection, and coupled to the electronic electrode switching/selection circuit or separately therefrom, either in the pacer neck, an adapter, or in the leads themselves.

DESCRIPTION OF THE PREFERRED EMBODIMENTS

Figure 1:
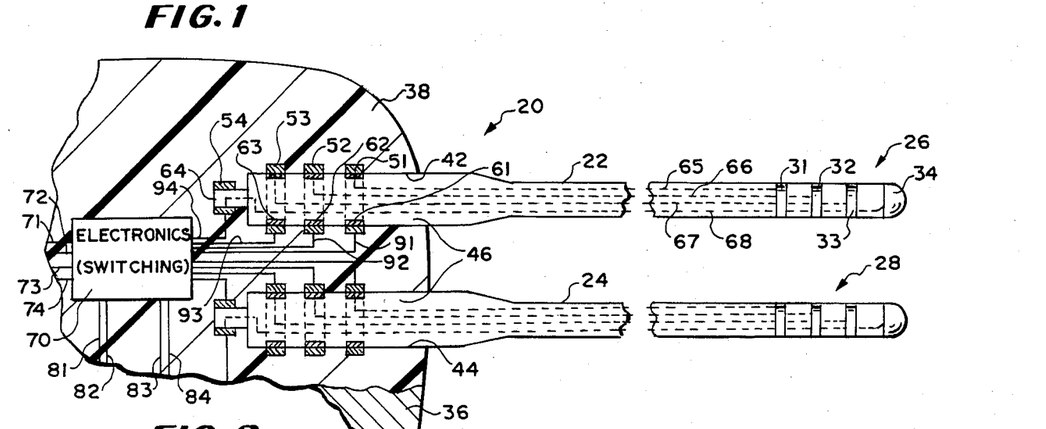
FIG. 1 is a partially schematic, partially mechanical view of a portion of a cardiac pacer and a pair of multielectrode leads connected thereto and shows the electronic electrode switching/selection circuitry of the present invention in the neck of the pacer.

Referring now to the drawings, and particularly to FIG. 1, there is shown and illustrated therein a cardiac pacemaker or pacer generally identified by reference numeral 20. The pacer 20 is adapted to be implanted in the body of a patient and to be connected electrically to the patient's heart by one or more, generally two, multielectrode leads 22 and 24 having tip electrode assemblies 26 and 28. The leads 22 and 24 can be sutured in position or, as indicated by the tip electrode assemblies 26 and 28, are pervenous leads which are fed through a vein to the interior of the patient's heart.

One of the leads, for example, the lead 22, may be led to the atrium of the heart and the other, for example, the lead 24, may be led to the ventricle. Then, in accordance with established procedures, electrodes 31-34 in each of the tip electrode assemblies 26 and 28 are tested, as for threshold, whereby the physician may make a determination as to which of the various electrodes 31-34 will be used for which of various pacer functions.

The electrode 34 is a tip electrode and electrodes 31-33 are ring electrodes.

Inasmuch as the spacing, type, and ultimate usage of the various electrodes 31-34 in each of the leads 22 and 24 do not form a part of the present invention, they are not described herein in detail. It will be sufficient to point out that the leads 22 and 24 may be identical, having the same number of sleeve or ring electrodes 31-33 or different, having a different number of sleeve electrodes and may be used for pacing or for sensing, or for both. Further, one or both may be unipolar, that is, where the pulse return path is, for example by way of a pacer case 36, or bipolar, that is, where the pulse path includes a pair of electrodes on the same lead.

Similarly, the pacer 20 may be of substantially any design and have programmable and microprocessor controlled circuitry therein. Accordingly, the pacer 20 will not be described further herein except to point out that such pacer 20 includes the hermetically sealed case 36 having a plurality of feedthroughs (not shown) bringing the pacing and sensing lead conductors through the hermetically sealed case 36 to a pacer neck 38 made of an insulative material. The case 36 is typically made of metal and the feedthroughs for conduction coupled to the pacing and sensing leads 22 and 24 extend through the case 36 and into the neck 38 to sockets 42 and 44 in the pacer neck 38. Each socket 42 and 44 receives a proximal connector 46 on one of the leads 22 or 24.

Each socket 42 or 44 is cylindrical in shape and has a plurality, e.g. three connector rings or sleeves 51, 52 and 53 mounted therein and a pin receiving metal socket connector 54. Each socket 42 or 44 receives one of the connectors 46 which has a plurality, e.g. three, connector sleeves 61, 62 and 63 adapted to contact the rings 51, 52 and 53 and a pin 64 which is received in the metal socket 54.

Each lead 22 and 24 has a tip electrode assembly 26 or 28 at the distal end thereof comprising three sleeve electrodes 31-33 and tip electrode 34, which are connected, respectively, by conductors 65, 66, 67 and 68 to sleeves 61, 62 and 63 and pin 64 as shown.

The neck 38 of the pacer 20 has mounted therein an electronic electrode switching/selection circuit 70 constructed according to the teachings of the present invention and having four output conductors 71-74 which extend through four feedthroughs (not shown) between the neck 28 and the case 36 for connection to pacer circuitry (not shown). Control lines 81-84 also extend through feedthroughs from the pacer circuitry and are connected to the switching/selection circuit 70.

Four input conductors 91-94 are connected, respectively, from each of the contact rings 51-53 and the connector socket 54 of each socket 42 and 44 to the switching/selection circuit 70 as shown.

The control lines 81-84 control the switching/selection circuit 70 for connecting selected "input" conductors 91-94 coupled to each socket 42 and 44 to selected "output" conductors 71-74.

The control lines 81-84 may be controlled by the pacer 20, directly or indirectly, or may be actuated or controlled by a number of other means, including additional programming circuitry. For example, a magnetic reed switch may be used to selectively actuate the control lines 81-84, as may radio-frequency or inductive coupling means. Similarly, if actuated by the pacer electronics, feedthroughs may be used therefor, or inductive or other indirect coupling may be used. The actuating or programming circuitry may be incorporated into the electronic circuitry of the electrode switching/selection circuit 70, if desired.

In accordance with the teachings of the present invention, selection may be made either by programming the electrode switching/selection circuit 70 by a pacer programmer and/or selection may be made by dynamically switching the control lines 81-84 and thereby the electrode switching/selection circuit 70 on a sampling basis by the control electronics of the pacer 20. The selection signal may, in the first stated instance, originate in the main pacer programming circuit or the electrode switching/selection circuit 70 may itself be capable of directly receiving programming signals from a programmer.

In addition, of course, power supply lines for the switches and control circuits, as needed, can also be supplied for the switching/selection circuit 70, but for clarity, these have not been shown. However, it will be apparent that the circuit 70 can be powered separately or by the main pacer power supply including being powered by a capacitor charged by the pacer by a multiplex arrangement through the feedthroughs. Also, as will be apparent hereinafter, zener protection diodes can be provided.

Figure 2:
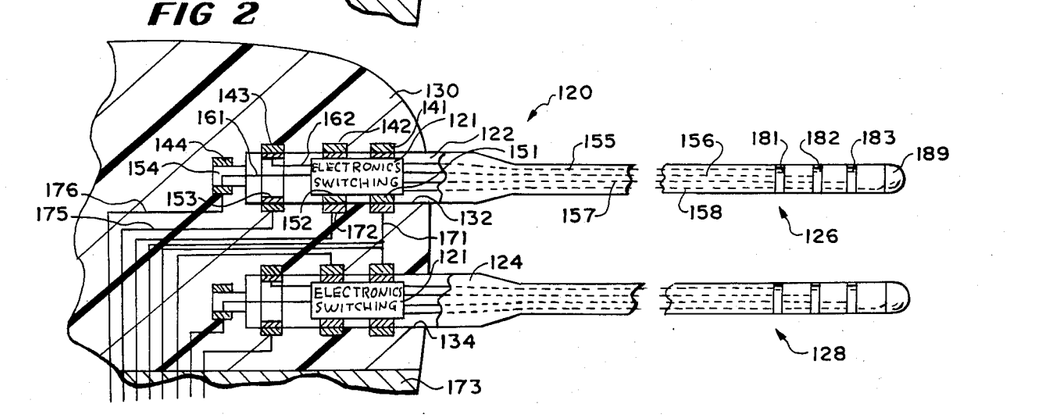
FIG. 2 is a partially schematic, partially mechanical view similar to the view shown in FIG. 1 and shows the electronic electrode switching/selection circuitry in the proximal connector assembly of each lead.

Referring now to FIG. 2, there is shown and illustrated therein another embodiment or modification of a pacer 120 wherein an electrode switching/selection circuit 121 of the present invention is built into proximal connectors 122 and 124 of multielectrode leads 126 and 128 rather than in a pacer neck 130.

The pacer neck 130 has sockets 132 and 134 which have connector contact rings 141-143 and a metal socket 144 therein for making contact with sleeves 151-153 and pin 154 on the connectors 122 or 124. Here all lead conductors 155-158 are connected to the switching/selection circuit 121 in each proximal connector 122, 124; and two input/output conductors 161 and 162 are connected to sleeve 153 and pin 154 while sleeves 151 and 152 provide control line connections to the switching/selection circuit 121.

Control lines 171 and 172 are connected to and extend in the neck 130 from the rings 141 and 142 (in contact with sleeves 151 and 152) through feedthroughs in a pacer case 173 to pacer electronics (not shown). Then, pacer electrode coupling conductors 175 and 176 are connected to and extend in the neck from ring 143 and socket 144 through feedthroughs in the pacer case 173 to pacer electronics.

Multielectrode lead connectors 122 and 124 are plugged into the sockets 132 and 134. An electronic electrode switching/selection circuit 121 is mounted in each connector 122, 124 and has control terminals comprising sleeves 151 and 152 (in contact with rings 141 and 142) and output/input lines defined by conductors 161 and 162 (connected to ring 143 and pin 154). Both ring 143 and pin 154 are in contact with a sleeve 153 or metal socket 144 connected to conductors 175, 176. The electrode switching/selection circuit 21 is effective to selectively connect each conductor 155-158 (connected to one of the four electrodes 181-184) to one of the conductors 175 or 176 with no additional electronics built into the pacer 120.

As stated above, zener protection diodes have heretofore been suggested for use in cardiac pacers to provide protection from potentially damaging high voltages, as may occur during electrosurgery, defibrillation, and the like. Such zener protection diodes, however, are conventionally incorporated into the internal pacer electronic circuitry.

In pacers constructed according to the teachings of the present invention, where additional circuitry is provided external to the hermetically sealed pacer case containing the pacer electronics, such internal zener protection diodes can provide only limited or incomplete protection. Ideally, for complete protection, the zener protection diodes should be coupled between lead conductors ahead of any of the circuitry in the pacer, i.e., closest to the electrodes, including the electrode switching/selection circuits 70 or 121 of the present invention, even though the electrode switching/selection circuits 70 or 121 are external to the pacer case 36 or 173 and even though the electrode switching/selection circuits 70 or 121 may be incorporated in a separate adapter or in the multielectrode leads 22, 24 or 126, 128 themselves. Further, such zener protection diodes may be used whether the leads 22, 24 or 126, 128 are arranged as unipolar, i.e., with the return from an electrode being via the pacer case, or bipolar, utilizing separate lead electrodes 31-34 or 181-184 for the active and return electric current paths.

Figures 3, 3A:
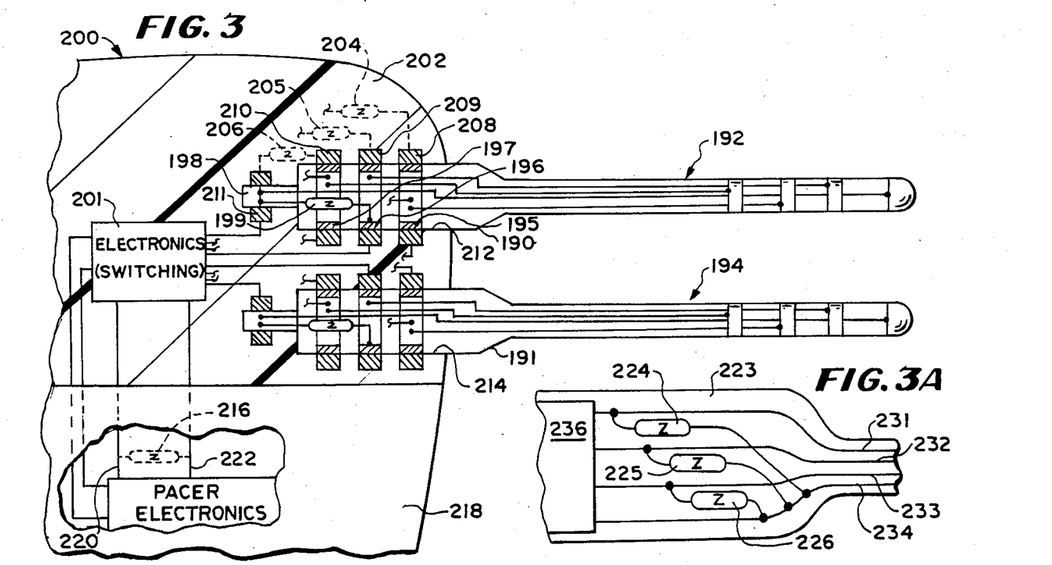
FIG. 3 is a partially schematic, partially mechanical view similar to the view shown in FIG. 1 and shows the location of zener protection diodes ahead of the pacer circuitry before or after the switching/selection circuitry in the pacer or in each proximal connector assembly of each lead.
FIG. 3A is a partially schematic, partially mechanical fragmentary view of a proximal connector and shows another arrangement of zener protection diodes therein.

Referring now to FIG. 3, a zener diode protection arrangement includes zener diodes in a proximal connector 190 or 191 of leads 192 or 194. Three zener diodes are provided connected between each connector sleeve 195, 196 or 197 and a pin 198. However, only one of the diodes, zener diode 199 is shown connected between sleeve 196 and pin 198. Here a pacer 200 has a switching/selection circuit 201 mounted in a pacer neck 202.

Alternatively, zener diodes 204, 205 and 206 shown in phantom can be connected between connector rings 208, 209 and 210 and a metal socket 211 in a socket 212 or 214 in the neck 202 which contact sleeves 195-197 and pin 198. Here the doides 204-206 are embedded in the neck 202. It will be readily apparent that the multielectrode leads 192, 194 are intended to be used in a bipolar mode.

If desired, zener protection diodes may be connected between the electrode lead conductors and ground, to enable the leads to be used in a unipolar mode.

Also shown in phantom in FIG. 3 is an internal zener protection diode 216 which, in the illustrated embodiment, would be redundant but which used alone would provide internal protection. Here the diode 216 is in a pacer case 218 between conductors 220 and 222 from the switching/selection circuit 201.

FIG. 3A is an enlarged, fragmentary view of a proximal lead connector 223 wherein zener diodes 224, 225 and 226 are connected between respective lead conductors 231-233 and lead conductor 234 before these conductors connect with a switching/selection circuit 236 mounted in the connector 223.

Referring now to FIGS. 4-7, there are illustrated therein adapters which have mounted therein switching/selection circuits, which are adapted to receive proximal lead connectors and which have a plug connector adapted to be received in a socket in a pacer neck. In this way, an electrode switching/selection circuit can be provided in the form of a separate component mounted in an adapter which is adapted to be installed between the pacer and a multielectrode lead.

Figure 4:
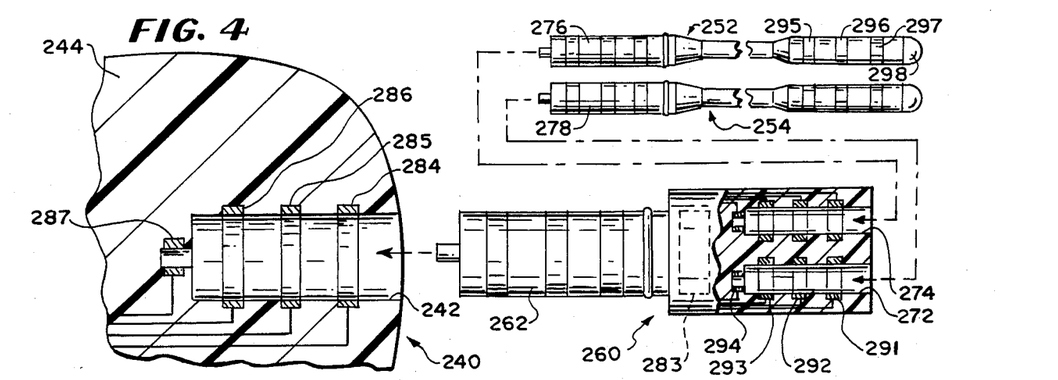
FIG. 4 is a partially schematic, partially mechanical view similar to the view shown in FIG. 1 and shows a pacer neck having a single lead socket, a plurality of multielectrode leads, an adapter adapted to be received in the pacer neck socket and the electronic electrode switching/selection circuitry built into the adapter.
Figure 5:
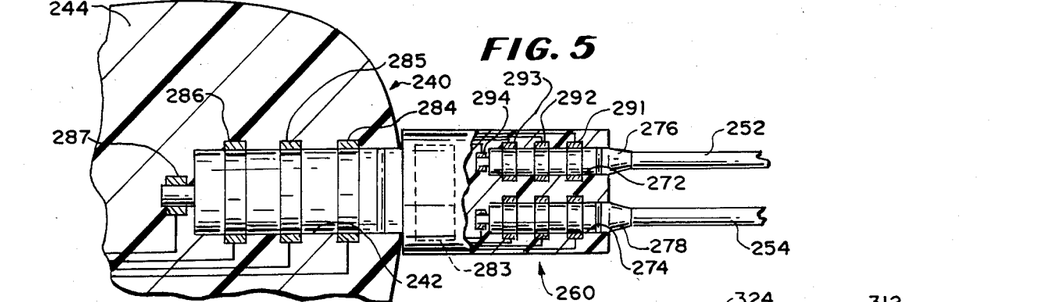
FIG. 5 is a partially schematic, partially mechanical view similar to the view shown in FIG. 4 and shows the multielectrode leads in the adapter and the adapter in the socket in the pacer neck.

Referring particularly to FIGS. 4 and 5, there is shown and illustrated therein a pacer 240, differing from the pacer 20 of FIG. 2 in that only a single socket 242 is provided in a pacer neck 244 of the pacer 240. A pair of multielectrode pacer leads 252 and 254, identical to the multielectrode leads 22 and 24 of FIG. 1 are adapted to be connected to the pacer 240 through an adapter 260. A plug connector 262 of the adapter 260 is adapted to be received in the pacer socket 242. Further, the adapter 260 has two sockets 272 and 274 which are adapted to receive proximal connectors 276 or 278 of multielectrode leads 252 or 254. The socket 242 and the sockets 272 and 274 can be the same size or different in size.

Within the adapter 260 is a switching/selection circuit 283 for selectively connecting connector rings 284, 285 or 286 or pin socket 287 in socket 242 with the connector rings 291, 292 or 293 or pin socket 294 in socket 272 or 274 in the adapter 260. Once assembled, as shown in FIG. 5, the electrode switching/selection circuit 283 will be interposed and operatively connected between the pacer 240 and the multielectrode leads 252 and 254 and the selection of electrodes 295, 296, 297 or 298 as desired may be carried out as in the previous described embodiments. Also, the adapter 260 can be provided with zener protection diodes similar to the zener protection diodes shown in FIGS. 3-3A.

Figures 6, 7:
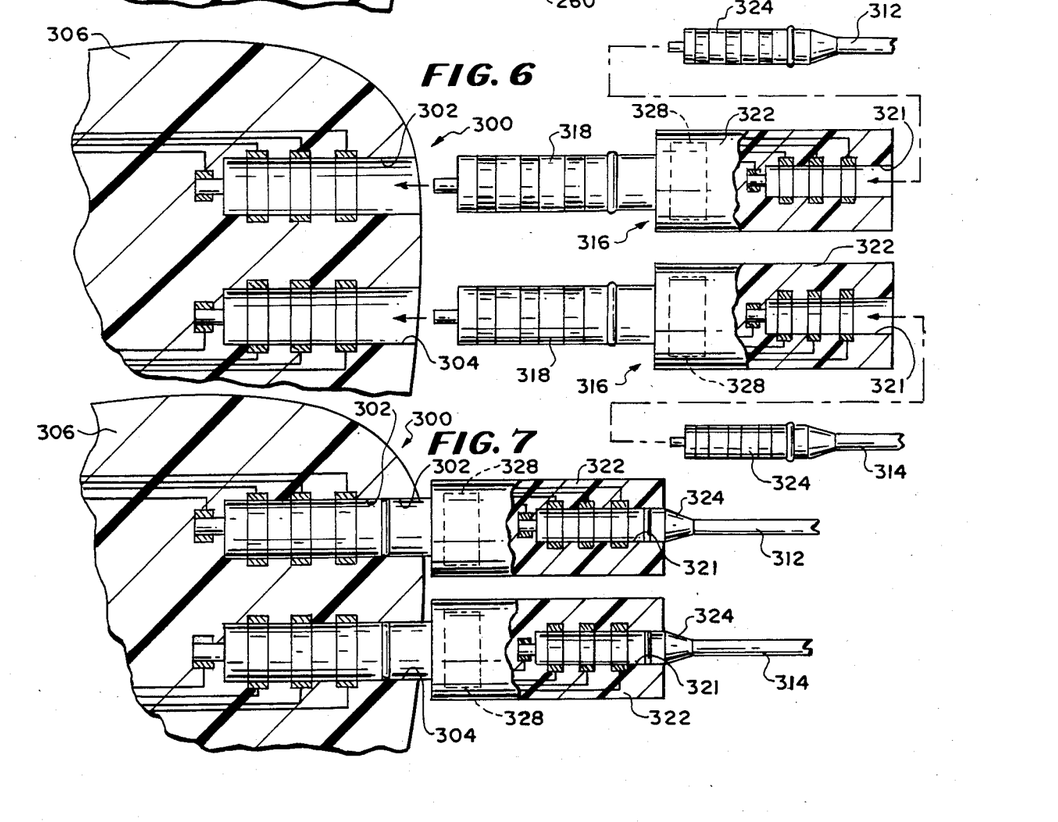
FIG. 6 is a partially schematic, partially mechanical view similar to the view shown in FIG. 4 and shows a pacer neck having two lead sockets, a separate adapter for each of the multielectrode leads adapted to be received in one of the sockets and electronic electrode switching/selection circuits built into each lead.
FIG. 7 is a partially schematic, partially mechanical view similar to the view shown in FIG. 5 and shows the leads in the adapters and the adaptersin the sockets.

Referring now particularly to FIGS. 6 and 7, there is shown and illustrated therein another pacer 300, differing from the pacer 240 of FIGS. 4 and 5 in that a pair of single sockets 302 and 304 are provided in a pacer neck 306. A pair of multielectrode pacer leads 312 and 314, identical to the multielectrode leads 252 and 254 shown in FIGS. 4 and 5, are connected by a pair of identical adapters 316, each including a plug connector portion 318 adapted to mate with and be received in one of the two sockets 302 and 304. Each adapter 316 has a socket 321 in a body portion 322 for receiving a proximal connector 324 of each lead 312 or 314. Each socket 321 is adapted to mate with and receive a proximal lead connector 324 of one of the multielectrode leads 312 and 314, as shown in the assembly illustration, FIG. 7.

Within the body portion 322 of each of the adapters 316 is mounted an electronic electrode switching/selection circuit 328 to enable selection of a particular electrode configuration desired for each of the multielectrode leads 312 and 314. Zener diode protection also can be provided as previously described.

The electronic electrode switching/selection circuits 70, 121, 201, 236, 283 or 328 may be implemented in a large number of ways. In view of the fact that they are to be implanted within the patient's body, however, they are preferably at least sealed or encapsulated. For small size, it is preferable that they be implemented in a microcircuit form, such as hybrid integrated circuits enclosed or encapsulated, for example, in electronic flat packs. A number of such implementations are shown and illustrated in FIGS. 8 through 12 and generally, these implementations are shown and illustrated in schematic form only. In the interest of keeping the drawings simple and clear, the power supply lines for the switches and control circuits have not been shown. It is to be expressly understood, however, that such power supply lines will be supplied as necessary. Moreover, it is also to be expressly understood that power may be supplied by any of a number of means and sources, including, by way of example and not by way of limitation, from the pacer directly, as by additional feedthroughs or multiplexing on the electrode feedthroughs, or indirectly, as by induction, or from a separate battery or bio-active generator, or, particularly if the implementation logic is appropriately selected so as to be non-volatile, from an external source, such as a programmer used during setting of the switching/selection circuit means.

Figure 8:
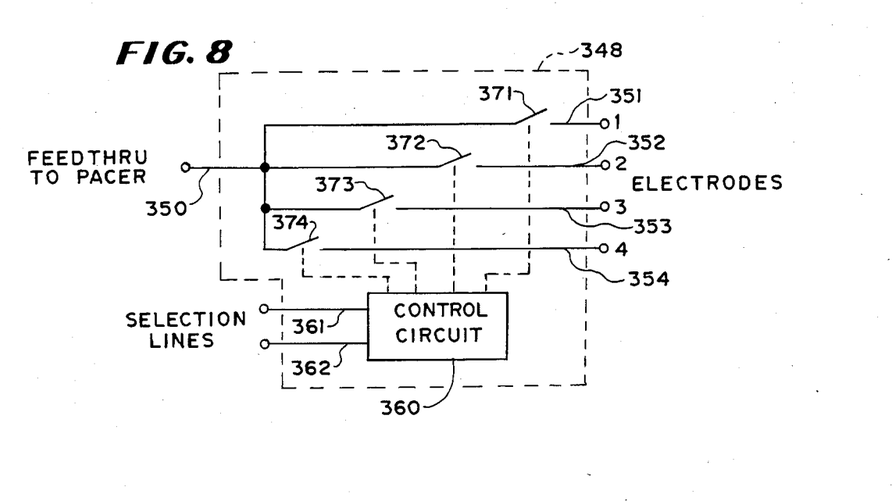
FIG. 8 is a schematic circuit diagram of one embodiment of the electronic electrode switching/selection circuitry of the present invention.
Figure 9:
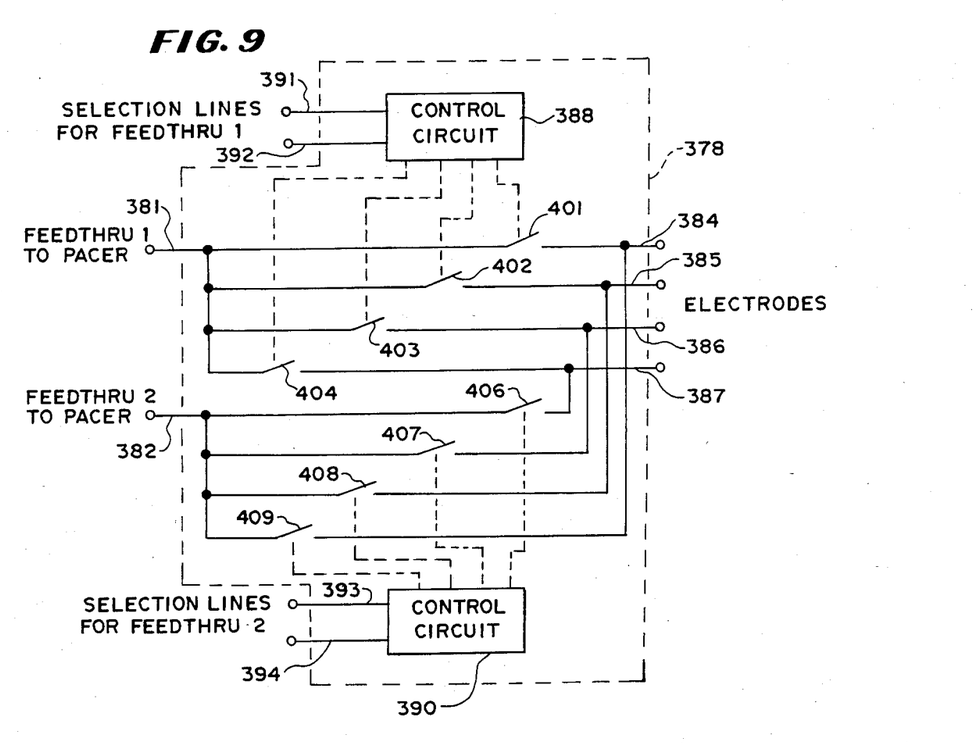
FIG. 9 is a schematic circuit diagram of another embodiment of the electronic electrode switching/selection circuitry of the present invention.

With particular reference now to FIGS. 8 and 9, switching circuits for 1 of 4 and 2 of 4 selection, respectively, are schematically illustrated in abstract form. It is to be expressly understood that the switches are only abstractly and schematically illustrated herein and any electric or electronic switches may be used and are intended. Preferably, the switches are electronic or solid state switches and may, for example, comprise bistable or monostable flip-flops, commercially packaged multiplexers, custom circuits, and FET's. Alternatively, and by way of further example and not limitation, the switches may comprise reed switches, particularly bistable magnetic reed switches.

In FIG. 8, there is shown and illustrated in abstract form an electronic electrode switching/selection circuit 348 wherein a single input lead conductor 350 is selectively coupled to any one of four output lead conductors 351-354. As used herein, the terms "input" and "output" are used only in relation to the circuits as shown in the drawings, reading from left to right, with the "input" to the left, and the "output" to the right, and also assuming for descriptive purpose only, that the circuit 348 is to handle a pacing pulse. It is to be expressly understood, however, that the intention is that sensing may also be switched or selected as desired. In this respect, the "input" and "output" would be reversed, when one of the four "sensing" conductors 351-354 is selectively connected with the pacer electronics through the conductor 350.

Accordingly, in either case, the circuit 348 comprises a 1 of 4 selector, selection being controlled by a control circuit or decoder/driver circuit 360 under binary control, for example, of selection or control lines 361 and 362 for driving or controlling four conductor coupling switches 371-374.

In FIG. 9, there is shown and illustrated in abstract form a similar electronic electrode switching/selection circuit means 378 including tandem switching to provide for selective switching of two input conductors 381 and 382 to four output leads 384, 385, 386, 387. Two control circuits or decoder/driver circuits 388, 390 under control of two sets of selection or control lines 391, 392, or 393, 394, respectively, are provided for the two input feedthrough conductors 381 and 382. The sets of selection or control lines 391-394 may, of course, be programmed through additional decoder/driver circuits to further reduce the number of conductors required for operating switches 401-404 or 406-409.

FIGS. 8 and 9, as heretofore pointed out, show, respectively, 1 of 4 and 2 of 4 selection. The switches of FIG. 8 and 9 may conveniently be implemented by MOS-FET switches having low ON and high OFF impedance. Commercial solid state integrated circuit packages are also available which may be used to implement the present invention.

Figure 10:
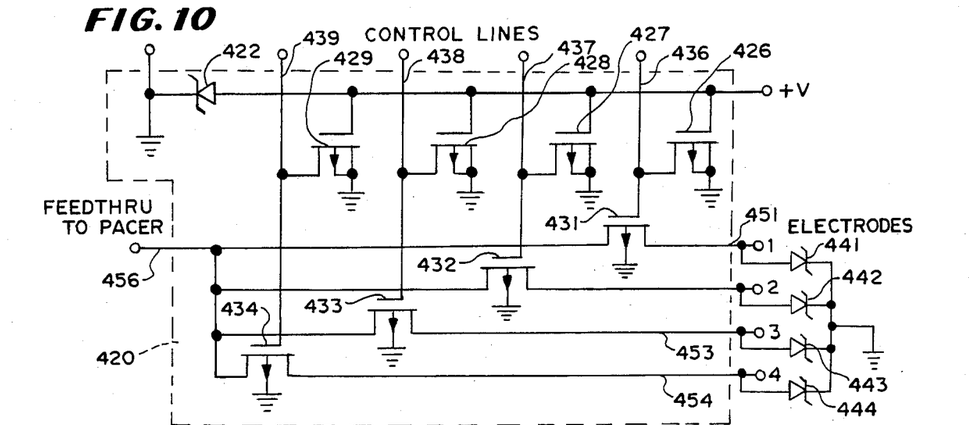
FIG. 10 is a schematic circuit diagram of another embodiment of the electronic electrode switching/selection circuitry of the present invention including field effect transistors.

For example, FIG. 10 shows a schematic circuit diagram of one implementation of a switching/selection circuit 420 using a commercially available solid state package. More specifically, FIG. 10 is a schematic circuit diagram of an Intersil G116MOS-FET selection switch package which includes circuitry to define electronic electrode/selection circuit 420. It will be noted that the G116 package contains a zener protection diode 422 and current generating FETS 426-429 which serve as active pullups for the FET switches 431-434 and which are coupled to control lines 436-439, respectively. Since the diode 420 would not provide complete protection, additional zener protection diodes 441-444 can be coupled to "output" conductors 451-454 for complete protection, as shown.

The control lines 436-439 control the connecting of an "input" lead conductor 456 to one of the "output" conductors 451-454.

Alternatively, there is commercially available a large assortment of so-called "analog switches" which may be used or which may be designed on a custom basis.

Figure 11:
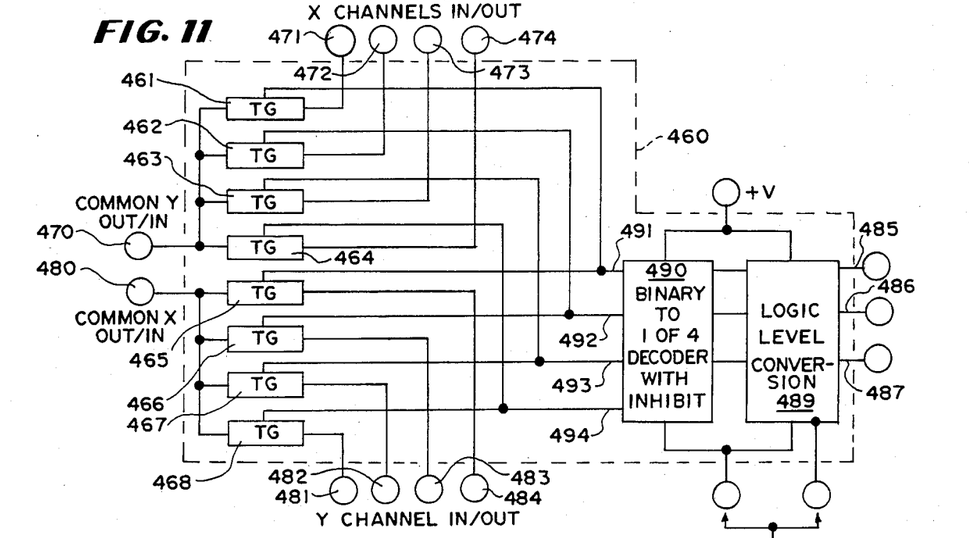
FIG. 11 is a schematic circuit diagram of another embodiment of the electronic electrode switching/selection circuitry of the present invention including an integrated circuit package.

For example, and with reference to FIG. 11, there is shown and illustrated therein a commercially available device from RCA, RCA CD4052B COS/MOS Analog Multiplexer/Demultiplexer suitable for 1 out of 4 selection. Here a switching/selection circuit 460 defined by the CD4052B device includes eight transmission gates "TG" 461-468 featuring low ON impedance and high OFF impedance. This device 460 can be used to implement the abstract 1 of 4 selection illustrated in FIG. 8 to define an electrode switching/selection circuit 460 in accordance with the present invention. Since this device is designed to switch both wires of a two-wire circuit, and pacer circuits are generally unbalanced to ground, only one channel is generally needed, for example, the Y channel with "input" 470 and "outputs" 471-474 as shown, and the X channel with "input" 480 and "outputs" 481-484 not used. Here three control line inputs 485-487 are provided connected to a Logic Level Conversion circuit 489 which has its output coupled to a Binary to 1 of 4 Decoder circuit 490 that has num output control lines 491-494 coupled to the TG's 461-464 and 465-468 for controlling opening or closing of same in response to logic levels on the inputs 485-487.

Figure 12:
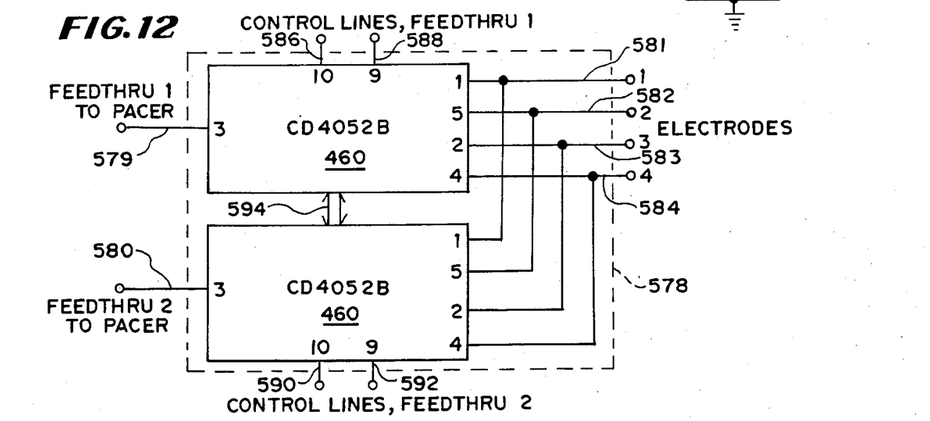
FIG. 12 is a schematic circuit diagram of yet another embodiment of the electronic electrode switching/selection circuitry of the present invention including plural integrated circuit packages enabling selection between plural feedthroughs and the multiple lead conductors.

FIG. 12 is a schematic circuit diagram of two CD4052B devices or switching/selection circuits 460 connected as abstractly schematically illustrated in FIG. 9 to define a 2 out of 4 selection switching/selection circuit 578 constructed according to the teachings of the present invention. Here "input" lead conductor 579 or 580 can be selectively connected to one of four "output" conductors 581-584. Logic levels on control lines 586 and 588 control connection of "input" conductor 579 to "output" conductors 581-584 and logic levels on control lines 590 and 592 control connection of "input" conductor 580 to "output" conductors 581-584. Priority of connections between "output" conductors 581-584 and "input" conductors 579 or 580 can be achieved by conventional "hand-shaking" or other prioritizing techniques via conductors 594 interconnecting the circuits 460. Of course, zener protection diodes may be added to the circuits 460 and 578 of FIGS. 11 and 12, respectively.

It should be recognized that the switching selection circuits disclosed herein will not result in minimization of feedthroughs in all cases. For example, two four electrode leads normally require eight feedthroughs. Selecting two electrodes from each lead, as illustrated above, may require four input/output feedthroughs, four selection/switching circuit control feedthroughs and two selection/switching circuit power feedthroughs, making a total of ten.

However, feedthrough savings will materialize as the number of electrodes increases, if the input/output feedthrough usage is multiplexed, if the switching/selection circuit is controlled or powered by means external to the pacer can or if the switching/selection circuit is controlled by serial sequence. The latter may be accomplished by means of, for example, a pulse-width modulated control sequence which, through a serial-to-parallel converter applies its output to the parallel control inputs of the switching/selection circuit.

Figure 13:
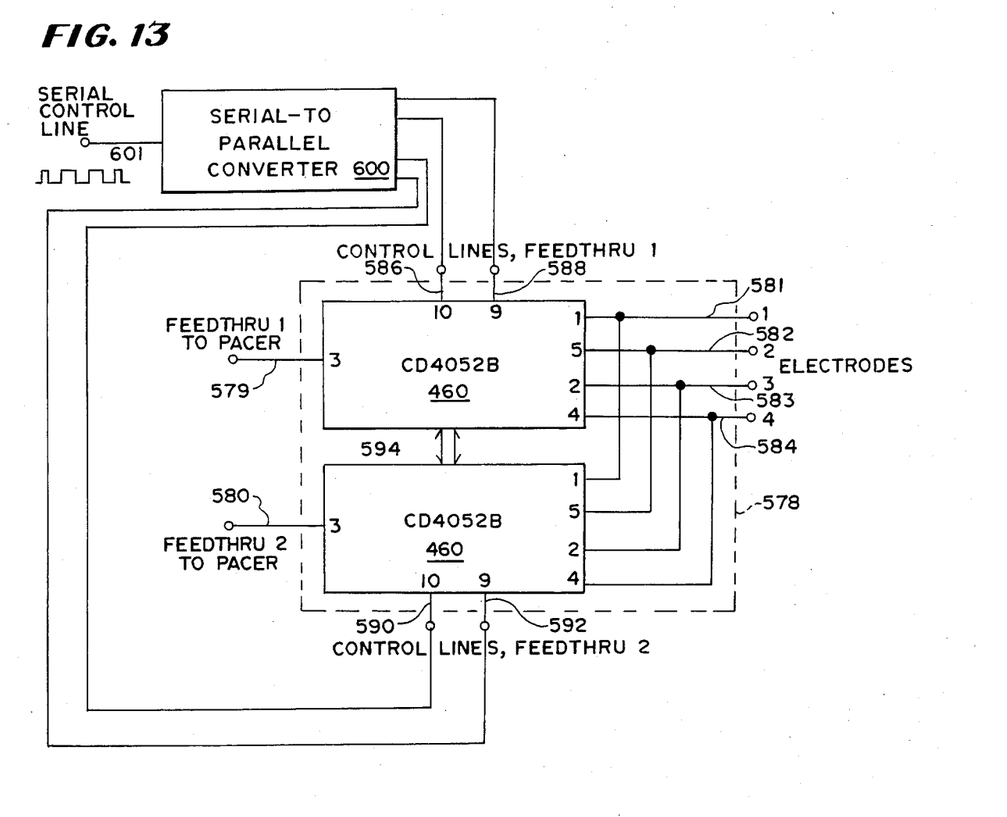
FIG. 13 is a schematic circuit diagram of the plural integrated circuit packages shown in FIG. 12 in combination with a serial-to-parallel converter.

In FIG. 13 there is schematically described above the switching/selection circuit 460 shown in FIG. 12 contained within the neck of the pacer along with a serial-to-parallel converter 600, also within the neck of the pacer (or in a lead or an adapter in accordance with the teachings of the present invention). A serial control line 601 with a pulse-width modulated control signal, is the only control line required to originate within the pacer can. Control lines 586, 588, 590 and 592 are generated from this signal.

In the example illustrated in FIG. 13 a signal burst of short, wide, wide, short may represent logic 0, 1, 1, 0 on lines 588, 586, 590 and 592 respectively.

Serial-to-parallel converter 600 may be implemented in various ways. A simple implementation is in the form of a shift register in which, for the example described above, four flip-flops store each serial four bit sequence as determined by a pulse-width demodulator. As a result, the four feedthroughs previously required for control lines 586, 588, 590 and 592 are replaced by a single feedthrough using the method described above.

From the foregoing description, it will be apparent that the switching/selection circuits 70, 121, 201, 236, 283, 328, 348, 378, 420, 460 and 578, the zener protection diode arrangements, and the pacer system in which they are used, of the present invention, provide a number of advantages, some of which have been described above and others of which are inherent in the invention. Most importantly, 1 to 4, 2 to 4 or 2 to 8 lead conductor selection is provided, thereby reducing the number of conductors in a pacer neck and the number of feedthroughs needed from the pacer neck to, through and into a pacer case. Also, various modifications can be made to the pacer system of the present invention without departing from the teachings of the present invention. Accordingly, the scope of the invention is only to be limited as necessitated by the accompanying claims.

We claim:

1. A cardiac pacing system including: a cardiac pacer having a sealed case with pacer electronic circuitry therein including a pacer system ground, a neck, and at least one feedthrough passing through the sealed case into the neck; a pacing lead having a proximal end portion which is received in said neck, a distal end portion, at least two electrodes in the distal end portion and at least two spaced apart terminal connectors in said proximal end portion, said at least one feedthrough being connectable to said terminal connectors, electrode switching/selection circuit means external to the sealed case and connected to said at least one feedthrough between said pacer electronic circuitry and said at least two electrodes for selectively electrically connecting one or more of the electrodes in the pacing lead through said at least one feedthrough with the pacer electronic circuitry.

2. The system of claim 1 further comprising a zener diode arrangement coupled between said pacer system ground and the side of said switching/selection circuit means connected to said electrodes.

3. The system of claim further comprising an adapter, said adapter including a plug connector portion which is received in a mating socket having ring connectors thereon and located in said pacer neck, and having a socket into which said proximal end portion of said multielectrode lead is received, said switching/selection circuit means being mounted within said adapter and being electrically connected between said plug connector portion and the ring connectors in said socket in said adapter.

4. The system of claim 3 further comprising a zener diode protection arrangement mounted within said adapter and coupled between conductors which extend from said switching selection circuit means to said ring conductors in said adapter socket.

5. The system of claim 1 wherein said switching/selection circuit means is built into said lead.

6. The system of claim 5 wherein said switching/selection circuit means is built into said proximal connector assembly in said proximal end portion of said lead.

7. The system of claim 5 further comprising a zener diode protection arrangement mounted within the lead and coupled between conductors which extend between the at least two electrodes and said switching/selection circuit means.

8. The system of claim 1 wherein said switching/selection circuit means is built into said pacer neck.

9. The system of claim 8 further comprising a zener diode protection arrangement comprising zener diodes mounted within said pacer neck and connected between conductors which extend from said switching/selection circuit means to the at least two electrodes.

10. The system of claim 9 wherein said zener diode protection arrangement includes a zener diode in said pacer between conductors extending from said switching/selection circuit means and said pacer electronic circuitry within said pacer case.

11. The system of claim 1 including a plurality of field effect transistor switches.

12. The system of claim 1 wherein said switching/selection circuit means comprises solid state electronic circuitry encased in a sealed package such as a so-called electronic flat pack.

13. The system of claim 1 wherein said switching/selection circuit means provides 1 to 4 conductor selection between four "output" conductors coupled to the lead electrodes and one "input" conductor extending from said switching/selection circuit means to and through said feedthrough.

14. The switching/selection circuit means of claim 13 including at least two control lines extending from said switching/selection circuit means to said and through feedthroughs extending into said pacer case for connection to pacer electronic circuitry in said pacer case.

15. The system of claim 1 wherein said switching/selection circuit means provides 2 to 8 conductor selection between four "output" conductors in one lead coupled to the lead electrodes and four "output" conductor in another lead coupled to the lead electrodes thereof and two "input" conductors extending to and through two of said feedthroughs.

16. The system of claim 15 including at least four control lines extending from said switching/selection circuit means to said and through feedthroughs extending into said pacer case for connection to pacer electronic circuitry in said pacer case.

17. The system of claim 15 further comprising two multielectrode pacing leads each having a proximal connector assembly and wherein said pacer neck has two sockets for receiving the proximal connector assemblies of the respective leads.

18. The system of claim 17 wherein said switching/selection circuit means is mounted in said pacer neck.

19. The system of claim 17 including two switching/selection circuit means each mounted in one of said proximal connector assemblies.

20. The system of claim 17 including two adapters and two switching/selection circuit means each mounted in one of said adapters and each adapter having a plug connector receivable in one of said pacer sockets and having a socket for receiving a lead proximal connector assembly.

21. The system of claim 15 in combination with the pacer and wherein said pacer neck has one socket and includes an adapter having one plug connector receivable in said pacer neck socket and having two sockets each for receiving a proximal connector at the proximal end of one multielectrode lead and wherein said switching/selection circuit means is mounted in said adapter.

22. The system of claim 1 including a plurality of transmission gates and binary logic control circuitry responsive to logic levels on input control lines thereto for controlling opening and closing of said respective transmission gates.

23. A method for limiting the number of feedthroughs required, for connection to a pacing lead having two or more distal electrodes, in a cardiac pacer, the pacer having a sealed pacer case with pacer circuitry therein, a pacer neck, and at least one feedthrough extending therethrough, said method comprising at least the steps of: providing a switching/selection circuit means external to the sealed pacer case for coupling the pacer circuitry with the pacing lead; and selectively electrically operating said switching/selection circuit means for selectively electrically connecting said pacer circuitry through said at least one feedthrough with one of the electrodes of the pacing lead.

24. The method of claim 23 wherein said step of selectively operating said switching/selection circuit means comprises programming said switching/selection circuit means to dedicate said at least one feedthrough to one of the electrodes of said multielectrode lead.

25. The method of claim 23 wherein said step of selectively operating said switching/selection circuit means comprises dynamically operating and switching/selection circuit means under control of the pacer circuitry.

26. A cardiac pacer system comprising a cardiac pacer unit having a sealed case containing pacer electronics, a pacer neck, and at least one feedthrough extending through said sealed case into said neck, a permanently implantable multielectrode pacing lead having at least two distal electrodes and being adapted to be connected to and used with said pacer unit, and electronic electrode switching/selection circuit means for selectively electrically coupling one or more of the electrodes of said multielectrode pacing lead with said pacer electronics through said at least one feedthrough.

27. The cardiac pacer system of claim 26 wherein said switching/selection circuit means provides a 1 to 4 selection between four electrodes and one feedthrough.

28. The cardiac pacer system of claim 26 wherein said switching/selection circuit means provides a 2 to 4 selection between eight electrodes and two feedthroughs.

29. The cardiac pacer system of claim 26 further comprising a zener protection diode arrangement external of said pacer case and coupled between conductors extending from the lead electrodes to said switching/selection circuit means.

* * * * *